(12) United States Patent
Isch et al.

(10) Patent No.: US 8,771,362 B2
(45) Date of Patent: Jul. 8, 2014

(54) VARIABLE ANGLE HUMERAL COMPONENTS

(71) Applicant: Biomet Manufacturing Corporation, Warsaw, IN (US)

(72) Inventors: Bryce A. Isch, Bluffton, IN (US); Nicholas J. Katrana, Fort Wayne, IN (US); Nathan A Winslow, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/653,844

(22) Filed: Oct. 17, 2012

(65) Prior Publication Data

US 2014/0107791 A1   Apr. 17, 2014

(51) Int. Cl.
*A61F 2/40* (2006.01)
*A61F 2/32* (2006.01)

(52) U.S. Cl.
USPC .................................... 623/19.14; 623/22.15

(58) Field of Classification Search
USPC ...................... 623/19.11–19.14, 23.11–23.38
See application file for complete search history.

(56) References Cited

U.S. PATENT DOCUMENTS

| | | | |
|---|---|---|---|
| 5,314,479 A | 5/1994 | Rockwood, Jr. et al. | |
| 5,613,971 A | 3/1997 | Lower et al. | |
| 6,248,132 B1* | 6/2001 | Harris | 623/22.15 |
| 6,663,670 B2 | 12/2003 | Rogers et al. | |
| 6,736,851 B2 | 5/2004 | Maroney et al. | |
| 6,749,637 B1 | 6/2004 | Baehler | |
| 6,986,790 B2 | 1/2006 | Ball et al. | |
| 7,011,686 B2 | 3/2006 | Ball et al. | |
| 7,097,663 B1 | 8/2006 | Nicol | |
| 7,195,645 B2 | 3/2007 | Disilvestro et al. | |

(Continued)

FOREIGN PATENT DOCUMENTS

| | | |
|---|---|---|
| DE | 10123517 C1 | 11/2002 |
| EP | 1920737 A2 | 5/2008 |

OTHER PUBLICATIONS

Joseph P. Ianotti, Steven B. Lippitt, and Gerald R. Williams, Jr., "Variation in Neck-Shaft Angle: Influence in Prosthetic Design", Supplement to The American Journal of Orthopedics, Dec. 2007, pp. 9-14.
Written Opinion of the International Searching Authority.

*Primary Examiner* — David Isabella
*Assistant Examiner* — Ann Schillinger
(74) *Attorney, Agent, or Firm* — Ryan O. White; Daniel J. Krieger; Taft Stettinius & Hollister LLP (57) ABSTRACT

A variable angle locking system comprising a humeral component having an underside at least partially defined by a cavity; a humeral stem couplable to the humeral component; a first washer defining a first through-hole and including a threaded portion; an adaptor defining a second through-hole and having a shelf portion and an elongated second washer, the shelf portion being adapted to be received by the cavity of the humeral component; a spring washer positioned between the first washer and the elongated second washer and defining a third through-hole; and a screw configured to lock the humeral component to the humeral stem at more than one angle relative to a common axis defined by the first, second and third through-holes, the screw including a head portion having helical threads and an elongated shaft portion extending from the head portion.

18 Claims, 10 Drawing Sheets

(56) References Cited

U.S. PATENT DOCUMENTS

| | | |
|---|---|---|
| 7,235,106 B2 | 6/2007 | Daniels et al. |
| 7,615,080 B2 | 11/2009 | Ondrla |
| 8,016,829 B2 | 9/2011 | Mahoney et al. |
| 2002/0120339 A1* | 8/2002 | Callaway et al. .......... 623/19.14 |
| 2003/0114933 A1* | 6/2003 | Bouttens et al. ........... 623/19.13 |
| 2004/0030400 A1 | 2/2004 | Horber |
| 2011/0106267 A1 | 5/2011 | Grant |
| 2012/0109321 A1 | 5/2012 | Stone et al. |
| 2012/0177462 A1 | 7/2012 | Fritzinger |

* cited by examiner

VARIABLE ANGLE HUMERAL COMPONENTS

TECHNICAL FIELD

The present invention generally relates to variable angle locking systems, and more particularly to variable angle humeral components.

BACKGROUND OF THE INVENTION

The statements in this section merely provide background information related to the present disclosure and should not be construed as constituting prior art.

Upon making a humeral resection during shoulder arthroplasty, variation may occur with respect to the angle of the humeral cut. If gross variation exists, unwanted clearance or impingement between the undersurface of the humeral head and the resected metaphyseal bone may occur. To address this issue, systems configured to compensate for angular variability can be used. While variable angle humeral head locking systems are commercially available, there is an ongoing need for humeral systems that not only allow for such angularly variability, but also satisfactorily accommodate both standard and eccentric humeral components.

The present invention is intended to improve upon and resolve some of the known deficiencies within the relevant art.

SUMMARY OF THE INVENTION

In accordance with one aspect of the present invention, a variable angle locking system is provided. According to this embodiment, the system comprises a humeral component having an underside at least partially defined by a cavity; a humeral stem couplable to the humeral component; a first washer defining a first through-hole and including a threaded portion; an adaptor defining a second through-hole, the adaptor including a shelf portion and an elongated second washer, wherein the shelf portion is adapted to be received by the cavity of the humeral component; a spring washer positioned between the first washer and the elongated second washer and defining a third through-hole; and a screw configured to lock the humeral component to the humeral stem at more than one angle relative to a common axis defined by the first, second and third through-holes, the screw including a head portion having helical threads and an elongated shaft portion extending from the head portion.

In accordance with yet another aspect of the present invention, the variable angle locking system comprises a humeral component; a humeral stem couplable to the humeral component; a set of stackable washers cooperating to create a common through-hole, the common through-hole defining a common axis therethrough; and a screw including a head portion having helical threads and an elongated shaft portion extending from the head portion, the screw being configured to lock the humeral component to the humeral stem at more than one angle relative to the common axis as the screw is advanced through the common through-hole. According to this embodiment, one of the at least three stackable washers is a spring washer.

In still another aspect of the present invention, the variable angle locking system comprises a set of stackable washers cooperating to create a common through-hole, wherein at least one of the washers in the set of stackable washers is a spring washer; a cap having a threaded circumference configured to engage an interior circumferential thread of one of the washers in the set of stackable washers; and a screw including a head portion having helical threads and an elongated shaft portion extending from the head portion, the screw being configured to lock a humeral component to a humeral stem at more than one angle relative to a common axis defined by the common through-hole as the screw is advanced therethrough. According to this embodiment, the cap is configured to cooperate with one of the washers in the set of stackable washers to collectively define a spherical cavity that is adapted to receive the head portion of the screw and at least a portion of the set of stackable washers.

Still other objects and benefits of the invention will become apparent from the following written description along with the accompanying figures.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Unless defined otherwise, all technical and scientific terms used herein have the same meaning as commonly understood by one of ordinary skill in the art to which this invention belongs. Although any method and materials similar or equivalent to those described herein can be used in the practice or testing of the present invention, the specific methods and materials are now described. Moreover, the techniques employed or contemplated herein are standard methodologies well known to one of ordinary skill in the art and the materials, methods and examples are illustrative only and not intended to be limiting.

Referencing generally FIGS. 1-4, a humeral component 100 for anatomically reconstructing a shoulder during an arthroplasty procedure is shown. In accordance with this illustrative aspect of the present invention, the humeral component 100 comprises a humeral head component 102 that may be variably angled with respect to a humeral stem 104. The humeral stem 104 is adapted to be received within the intramedullary canal of a humerus after the proximal portion of the humerus is resected, thereby exposing the intramedullary canal. In order to provide angular adjustment in both the sagittal plane and the coronal plane, the humeral head 102 is coupled to the humeral stem 104 using an adaptor 106.

In accordance with one aspect of the present invention, the adaptor 106 includes a shelf portion 108 and a fixation peg 110. The shelf portion 108 is configured to be received within a cavity 112 that is formed on the underside of the humeral head 102. Relative movement between the shelf portion 108 and the humeral head 102 is inhibited after the adaptor 106 and head 102 are secured via a friction fit.

In accordance with certain aspects of the present invention, the shelf portion 108 of the adaptor 106 comprises a taper body 114 defined by a bore or through-hole 116 that extends from a top planar surface 118 to a bottom planar surface 120 along a central axis. The bottom planar surface 120 abuts the circumferential face defined by the cylindrical body 114 and extends generally in parallel to the top surface 118. In accordance with certain embodiments herein, an arcuate inner wall 122 proximate the bottom surface 120 partially defines the through-hole 116 and flares outwardly as the axial distance from the bottom surface 120 increases. As will be discussed in more detail below, the arcuate inner wall 122 is adapted to receive at least a portion of the fixation peg 110 and allow the angle between the fixation peg and the shelf portion 108 to be changed.

As will be explained in more detail below, in accordance with certain aspects of the present invention, the fixation peg 110 functions as a washer that comprises an elongated stem 124 with a generally circular axial cross-section that tapers from a proximal end 126 to a distal end 128. The proximal end 126 of the fixation peg 110 includes a circumferential lip 130 that defines the circumferential boundary of the peg. The lip 130 abuts a circumferential surface 132 that diametrically tapers from the proximal end 126 to the distal end 128. In accordance with this illustrative embodiment, the distal end 128 includes a substantially planar bottom surface 134 that is generally parallel to a top surface 136. The top surface 136, however, includes an axially centered opening 138 that extends throughout the interior of the fixation peg 110 to define an internal bore. In accordance with certain aspects of the present invention, the axially centered opening 138 can be partially or fully threaded to mate with the threads of a locking screw 152 as it is installed thereto.

During installation, the adaptor 106 is configured to receive a threaded cap 140 having a threaded circumference to engage an interior circumferential thread 142 of the shelf portion 108 to secure the threaded cap to the shelf portion of the adaptor via a friction fit after a predetermined rotational movement. The threaded cap 140 includes a through-hole 144, at least partially defined by an inner concave circumferential wall 146, thereby forming a distal concavity. This distal concavity is sized to allow rotational and axial movement of components of the variable angle assembly. In particular, the dimensions of the circumferential wall 146 may be similar to the dimensions of the arcuate inner wall 122 partially defining the through-hole 116 of the adaptor 106. In this manner, the walls 122, 146 may cooperate to partially define a cavity when the threaded cap 140 is mounted to the shelf portion 108 of the adaptor 106. While not required herein, in accordance with certain aspects of the present invention, the cavity created by the cooperating walls 122, 146 may be substantially spherical in shape. As will be explained in more detail below, during assembly, this cavity is partially occupied by a top washer 148 and the lip portion 130 of the fixation peg 110.

To achieve angular variability in accordance with certain aspects of the present invention, the top washer 148 and lip portion 130 of the fixation peg 110 are inserted inside the cavity defined by the walls 122, 146 and a locking screw 152 is inserted into the opening 138 such that a portion of the screw is threaded into the top washer 148, while another portion of the screw is left resting on the top surface 136 of the fixation peg 110.

Figure 1:
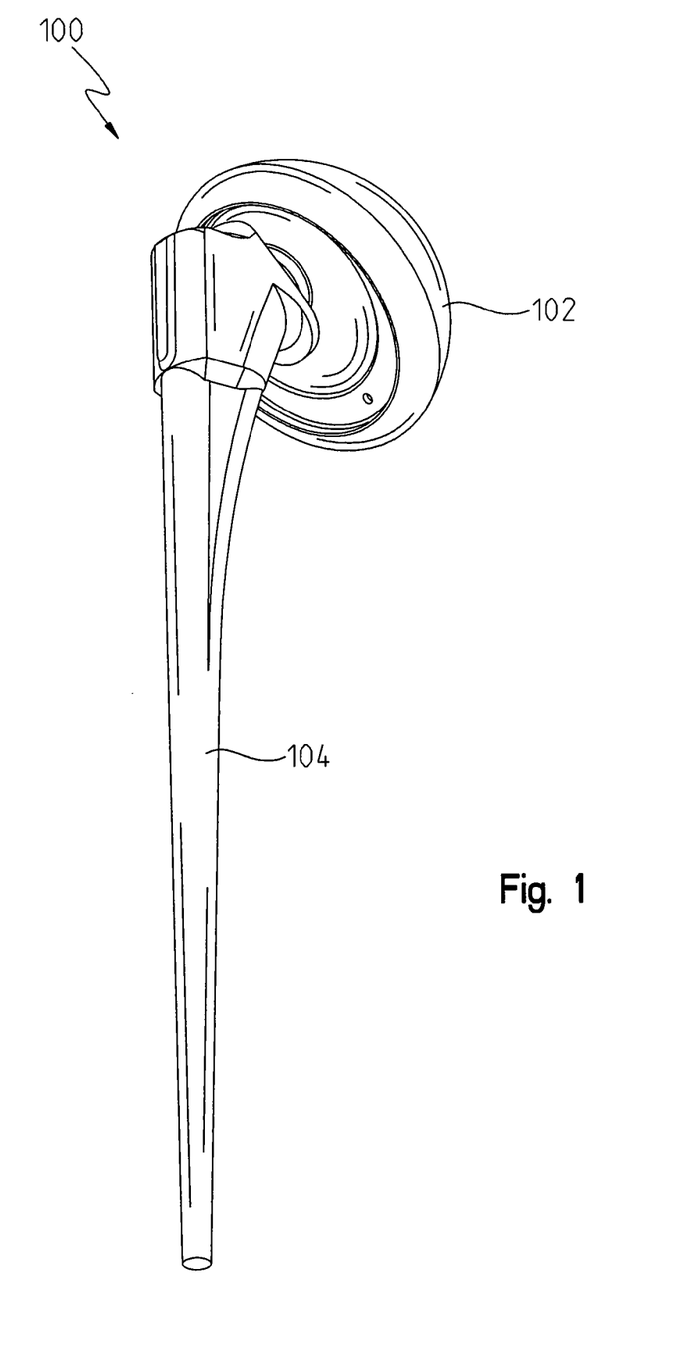
FIG. 1 illustratively depicts a perspective view of a variable angle locking humeral component in accordance with the teachings of the present invention.
Figure 2:
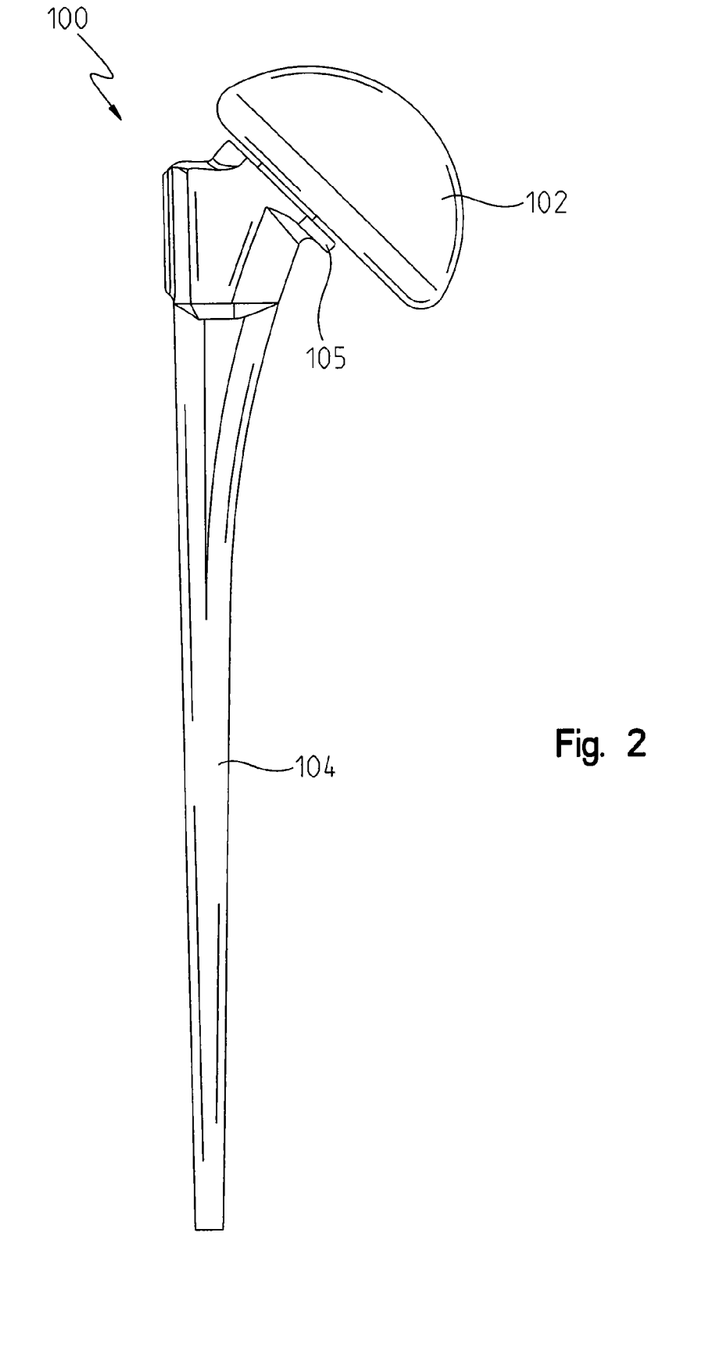
FIG. 2 illustratively depicts a side view of the variable angle locking humeral component of FIG. 1.
Figure 3:
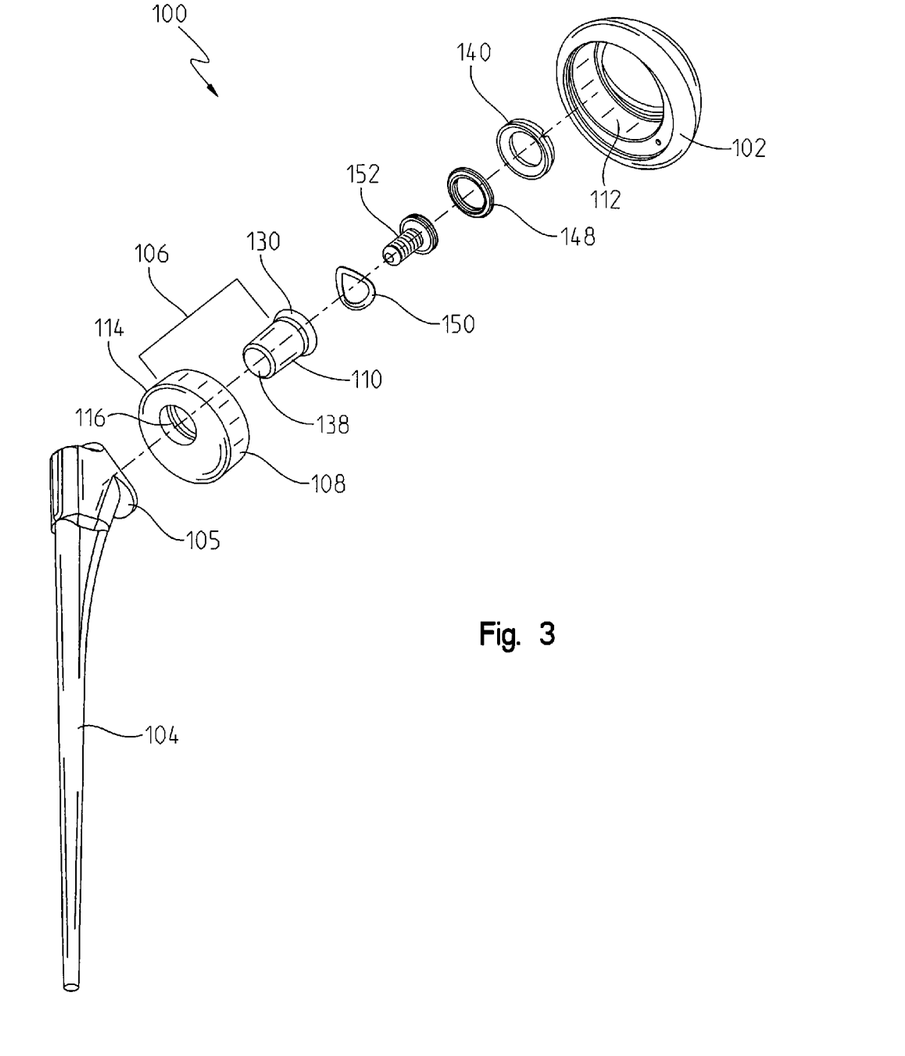
FIG. 3 illustratively depicts a perspective exploded view of the variable angle locking humeral component of FIG. 1.
Figure 4:
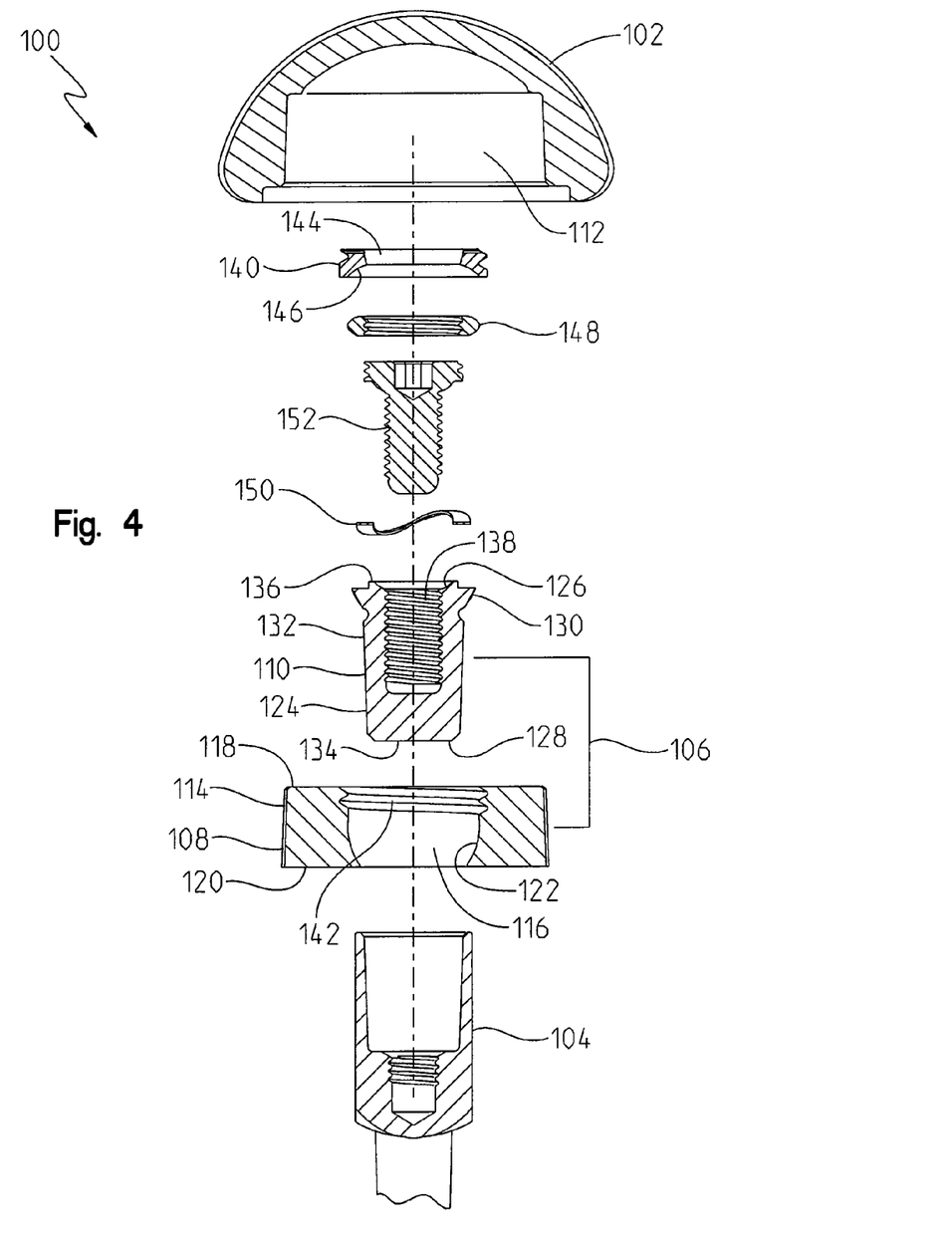
FIG. 4 illustratively depicts a front cross-sectional exploded view of the variable angle locking humeral component of FIG. 1.
Figure 5:
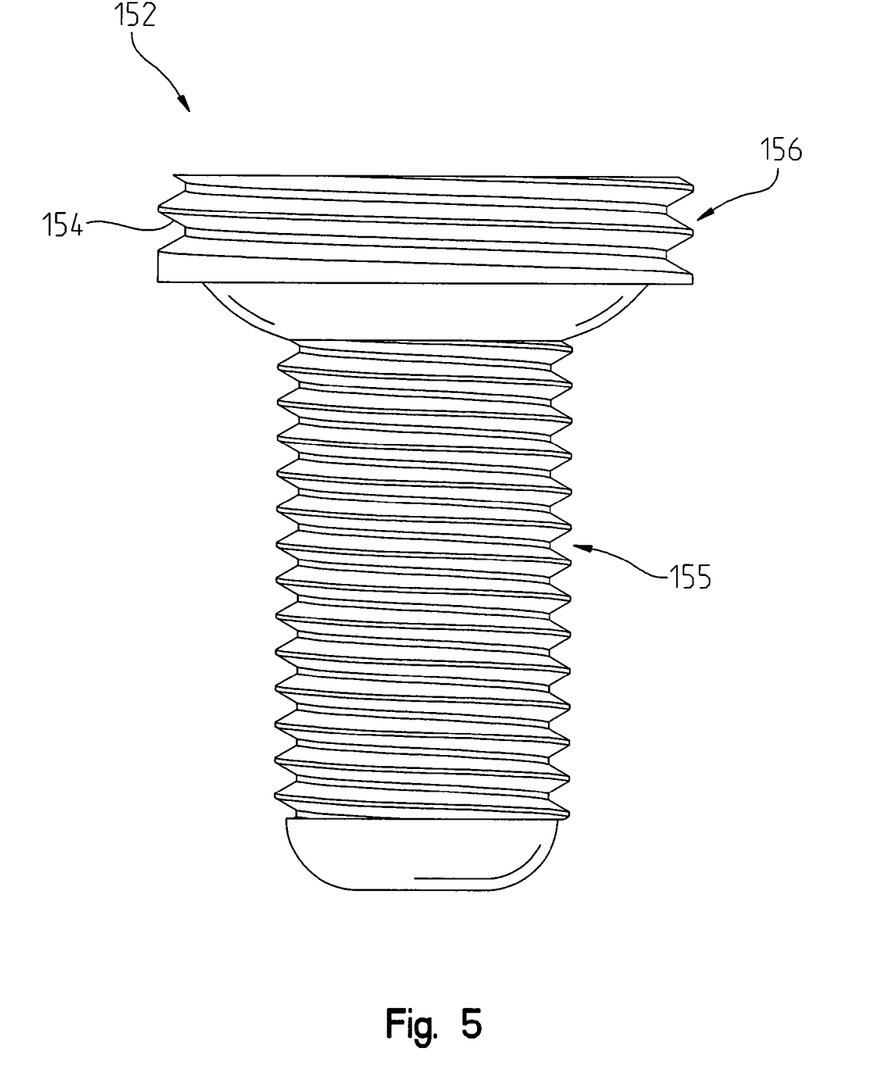
FIG. 5 illustratively depicts a front view of a locking screw for use with the variable angle locking humeral components of the present invention.

As shown particularly in FIG. 5, in accordance with certain aspects of the present invention, the locking screw 152 has helical threads 154 extending around the circumference of its head 156 and an elongated shaft portion 155 extending from the head portion. In certain aspects of the present invention, the elongated shaft portion 155 can be fully or partially threaded so that it can mate with the threads of the axially centered opening 138 of the fixation peg 110. Moreover, and depending on the use and application of the locking screw 152, it should also be understood and appreciated that the helical threads of the head portion 156, as well as threads of the elongated shaft portion 155, may be spherical, conical or spherical-conical in thread form.

In accordance with certain illustrative embodiments of the present invention, to assemble the humeral component 100, the top washer 148 is pre-loaded on top of the lip portion 130 of the fixation peg 110 and the screw head 156 is then initially threaded into the top washer 148. When the bottom of the screw head 156 meets the top surface 136 of the fixation peg 110 as the screw 152 is tightened, continued screw rotation will cause the top washer 148 and the fixation peg 110 to separate and push against the walls 122, 146 of the spherical cavity.

In addition to the top washer 148 and the bottom washer defined by the fixation peg of the adaptor 110, a middle washer 150 (assembled between the top and bottom washers) is also used in accordance with certain aspects of the present invention. In accordance with these illustrative embodiments, the middle washer 150 is a helical washer, a Belleville washer, a wave spring washer or a helical coil and is configured to provide a tensile force between the top and bottom washers 148, 110, thereby creating friction between the outer surface of the washers and the inner walls 122, 146 of the spherical cavity. The friction created provides an anti-rotational force, which in turn keeps the top washer 148 from turning as the helical threads 154 of the screw head 156 engage into the top washer 148. The anti-rotational force associated with such an arrangement advantageously minimizes or eliminates the need to utilize an additional instrument to keep the top washer 148 stationary. Moreover, the tensile force applied from the locking screw 152 to the top washer 148 also creates a mechanical lock between the construct, thereby locking the fixation peg/bottom washer 110 at a given trajectory. Once the trajectory of the fixation peg/bottom washer 110 is locked, the entire construct can be assembled into the humeral head component 102. While not shown in this illustrative embodiment, it should be understood herein that cutouts may be machined into the bottom planar surface 120 of the shelf portion 108 of the adaptor 106 to facilitate the collar portion 105 of the humeral stem 104 as the trajectory of the adaptor increases.

Because there are instances where it may be necessary to angularly or directionally adjust and lock the humeral head component 102 with respect to the humeral stem 104 (i.e., to adjust the inclination and/or version angle) to achieve a position that provides the most stability to the joint, thereby preventing dislocation, it is advantageous to provide a mechanism that allows the locking screw 152 to be oriented at angles and rotational positions off-axis (i.e., non-collinearly) to the axis 160 defined by the through-hole 116. To accomplish this angular variability, in accordance with certain aspects of the present invention, the inner walls 122, 146 of the spherical cavity can be machined in such a way that a mating pocket is created for holding the set of washers (110, 150 and 148) in place when the screw 152 is tightened thereto. While those of skill in the art will understand and appreciate that the size of the spherical cavity is directly related to the range of angularity to which the screw 152 can be installed into the adaptor 106, it is particularly useful if the mating pocket is shaped in such a manner that the washers are prevented from spinning when the screw is tightened. One exemplary way to prevent the washers from spinning is to size the washers such that they are slightly thicker than the mating pocket when in its free state. Another such exemplary option for preventing the washers from spinning is to create a light interference pressfit between the washers and the spherical cavity. Those of skill within the art will understand and appreciate that there are several ways to achieve such an interference press-fit relationship, however, in accordance with certain aspects of the present invention, the outer surfaces of the washer and/or through-hole could be roughened, serrated or knurled.

Figure 6:
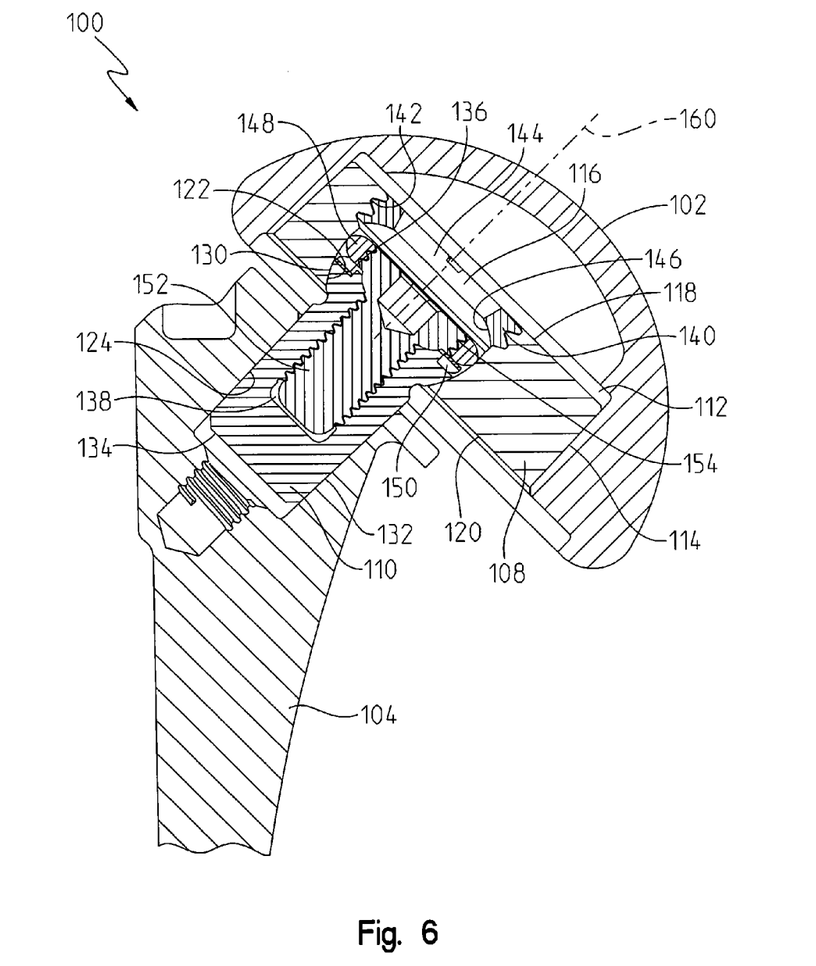
FIG. 6 illustratively depicts a cross-sectional view of the humeral head portion of a variable angle locking humeral component having an on-axis assembly in accordance with the teachings of the present invention.
Figure 7:
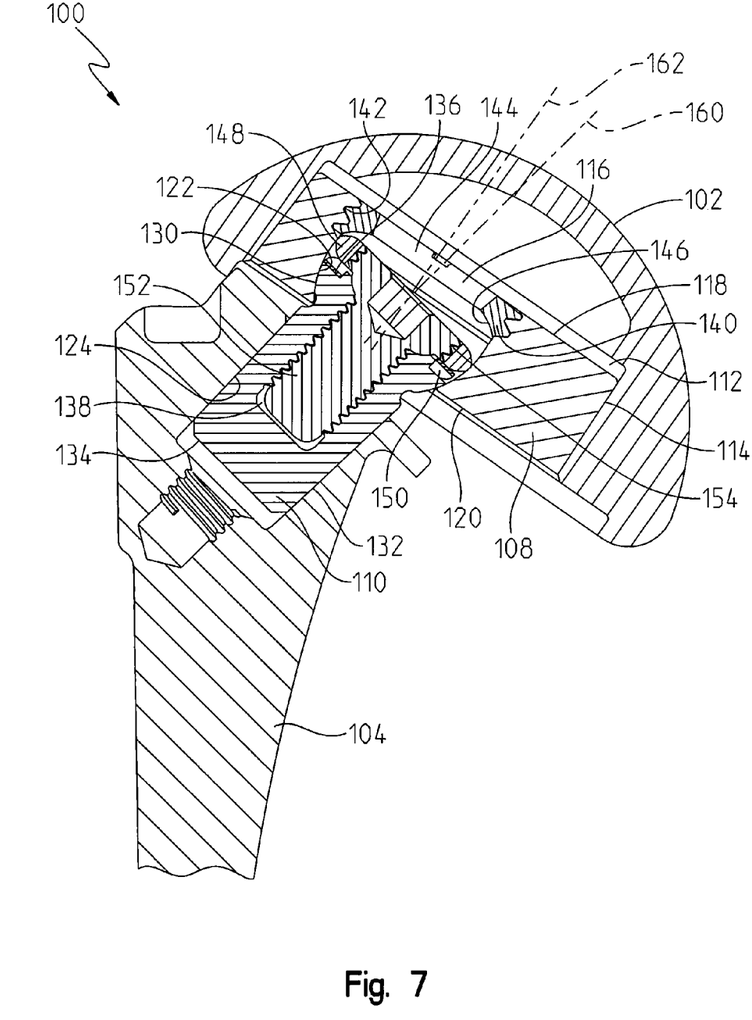
FIGS. 7-9 illustratively depicts the angularly variability associated with the humeral head portion of a variable angle locking humeral component in accordance with the teachings of the present invention.
Figure 8:
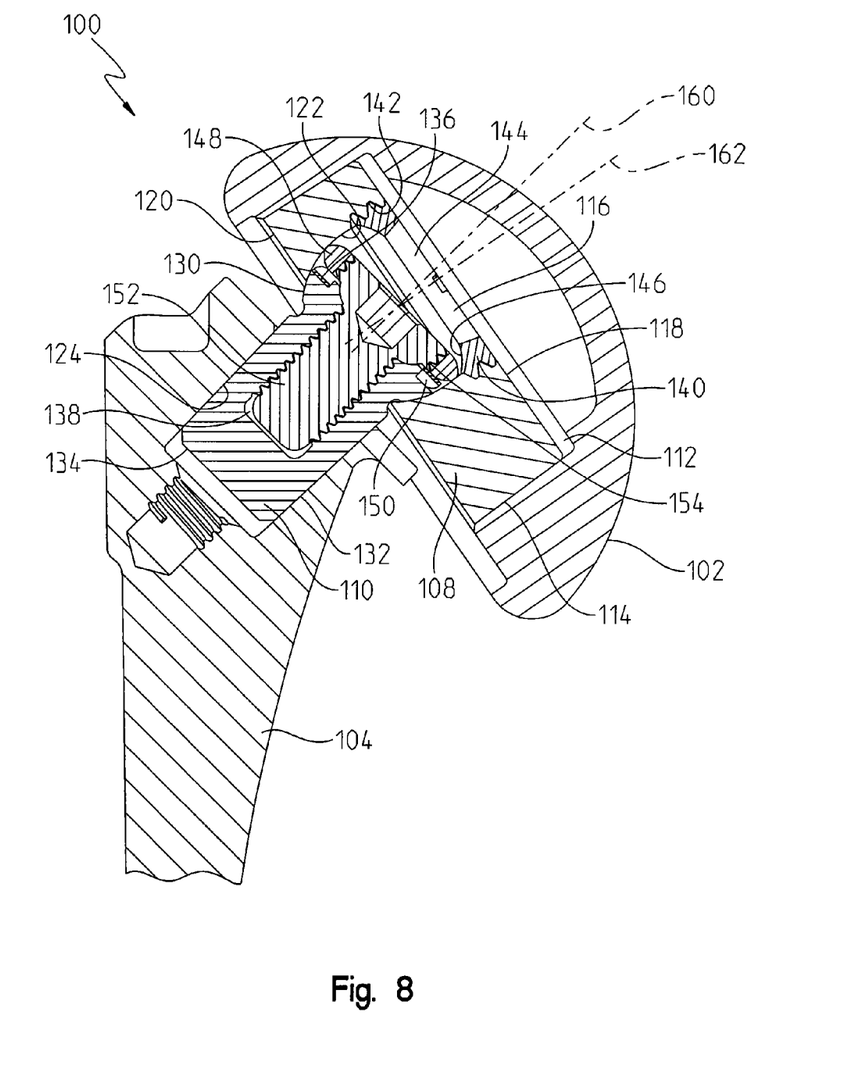
Figure 9:
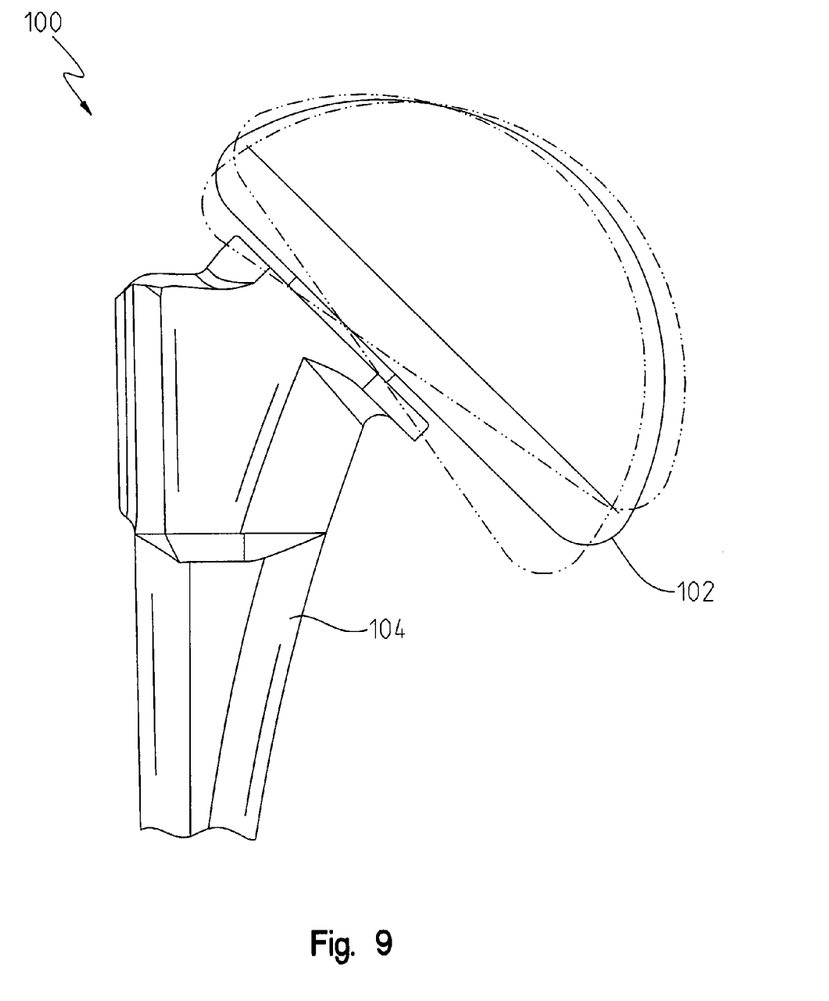

The angular variability permitted in accordance with the present invention can be particularly appreciated with reference to FIGS. 6-9. FIG. 6 shows the humeral head component 102 installed to the humeral stem 104 at an angular trajectory that is on-axis or collinear to the axis 160 defined by the through-hole 116. FIGS. 7 and 8, on the other hand, show the version angle variability of the humeral head component 102 by having it installed to the humeral stem 104 at an angular trajectory (see the axis represented by reference numeral 162) that is off-axis or non-collinear to the axis 160 defined by the through-hole 116. The angular variability (i.e., inclination angle) that is achievable in accordance with certain aspects of the present invention can be further appreciated with reference to FIG. 9 (see the adjustability of the humeral head component 102 represented by the dashed lines). In certain specific embodiments, the humeral head component 102 can be installed to the humeral stem 104 such that up to +/−15 degrees of version and inclination variability can be achieved to restore individual patient anatomy.

Figure 10:
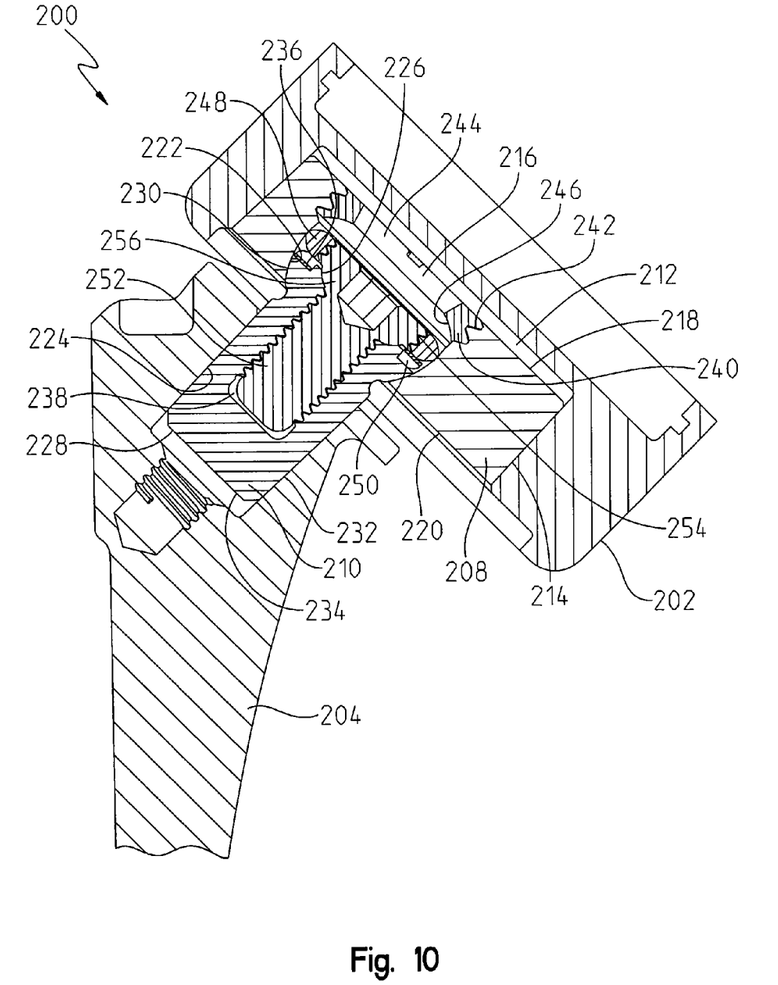
FIG. 10 illustratively depicts a cross-sectional view of an alternative variable angle locking humeral component in accordance with the teachings of the present invention.

Moving now to FIG. 10, an alternative variable angle locking humeral component 200 in accordance with the teachings of the present invention is illustrated. More particularly, the humeral head component 200 according to this embodiment is a locking reverse humeral tray that allows for adjustment of inclination and/or version angle. As those of skill in the art will understand and appreciate herein, such a variable angle locking system provides the ability to adjust the humeral articulation into a position that provides the most stability in the joint, thereby preventing dislocation. Such variability is particularly useful when converting a total shoulder or hemiarthroplasty to a reverse shoulder arthroplasty with a wellfixed stem that was positioned during the original procedure into more anteversion or retroversion than is desired for the reverse shoulder procedure. The ability to vary the humeral tray/inclination in accordance with this aspect of the present invention allows for the surgeon to compensate for the stem position.

In accordance with this illustrative aspect of the present invention, the humeral component 200 comprises a reverse tray component 202 that may be variably angled with respect to a humeral stem 204. In order to provide angular adjustment in both the sagittal plane and the coronal plane, the reverse tray component 202 is coupled to the humeral stem 204 using an adaptor having a shelf portion 208 and a fixation peg 210. The shelf portion 208 is configured to be received within a cavity 212 that is formed on the underside of the reverse tray component 202. Relative movement between the shelf portion 208 and the reverse tray component 202 is inhibited after the adaptor and reverse tray component 202 are secured via a friction fit.

The shelf portion 208 of the adaptor comprises a hollow cylindrical body 214 defined by a bore or through-hole 216 that extends from a top planar surface 218 to a bottom planar surface 220 along a central axis. The bottom planar surface 220 abuts the circumferential face defined by the cylindrical body 214 and extends generally in parallel to the top surface 218. In accordance with certain embodiments herein, an arcuate inner wall 222 proximate the bottom surface 220 partially defines the through-hole 216 and flares outwardly as the axial distance from the bottom surface 220 increases. The arcuate inner wall 222 is adapted to receive at least a portion of the fixation peg 210 and allow the angle between the fixation peg and the shelf portion 208 to be changed.

In accordance with certain aspects of the present invention, the fixation peg 210 functions as a washer that comprises an elongated stem 224 with a generally circular axial crosssection that tapers from a proximal end 226 to a distal end 228. The proximal end 226 of the fixation peg 210 includes a circumferential lip 230 that defines the circumferential boundary of the peg. The lip 230 abuts a circumferential surface 232 that diametrically tapers from the proximal end 226 to the distal end 228. In accordance with this illustrative embodiment, the distal end 228 includes a substantially planar bottom surface 234 that is generally parallel to a top surface 236. The top surface 236, however, includes an axially centered opening 238 that extends throughout the interior of the fixation peg 210 to define an internal bore. In accordance with certain aspects of the present invention, the axially centered opening 238 can be partially or fully threaded to mate with the threads of a locking screw 252 as it is installed thereto.

During installation, the adaptor is configured to receive a threaded cap 240 having a threaded circumference to engage an interior circumferential thread 242 of the shelf portion 208 to secure the threaded cap to the shelf portion of the adaptor via a friction fit after a predetermined rotational movement. The threaded cap 240 includes a through-hole 244, at least partially defined by an inner concave circumferential wall 246, thereby forming a distal concavity. This distal concavity is sized to allow rotational and axial movement of components of the variable angle assembly. In particular, the dimensions of the circumferential wall 246 may be similar to the dimensions of the arcuate inner wall 222 partially defining the through-hole 216 of the adaptor. In this manner, the walls 222, 246 may cooperate to partially define a spherical cavity when the threaded cap 240 is mounted to the shelf portion 208 of the adaptor. As will be explained in more detail below, during assembly, this spherical cavity is partially occupied by a top washer 248 and the lip portion 230 of the fixation peg 210.

To achieve angular variability in accordance with certain aspects of the present invention, the top washer 248 and lip portion 230 of the fixation peg 210 are inserted inside the spherical cavity defined by the walls 222, 246 and a locking screw 252 is inserted into the opening 238 such that a portion of the screw is threaded into the top washer 248, while another portion of the screw is left resting on the top surface 236 of the fixation peg 210.

In addition to the top washer 248 and the bottom washer defined by the fixation peg of the adaptor 210, a middle spring washer 250 (assembled between the top and bottom washers) is also used in accordance with certain aspects of the present invention. In accordance with these illustrative embodiments, the spring washer 250 is configured to provide a tensile force between the top and bottom washers 248, 210, thereby creating friction between the outer surface of the washers and the inner walls 222, 246 of the spherical cavity. The friction created provides an anti-rotational force, which in turn keeps the top washer 248 from turning as helical threads 254 of the screw head 256 engage into the top washer 248. The anti-rotational force associated with such an arrangement advantageously minimizes or eliminates the need to utilize an additional instrument to keep the top washer 248 stationary. Moreover, the tensile force applied from the locking screw 252 to the top washer 248 also creates a mechanical lock between the construct, thereby locking the fixation peg/bottom washer 210 at a given trajectory. Once the trajectory of the fixation peg/bottom washer 210 is locked, the entire construct can be assembled into the reverse tray component 202. While not shown in this illustrative embodiment, it should be understood herein that cutouts may be machined into the bottom planar surface 220 of the shelf portion 208 of the adaptor to facilitate the collar portion 205 of the humeral stem 204 as the trajectory of the adaptor increases.

Because there are instances where it may be necessary to angularly or directionally adjust and lock the reverse tray component 202 with respect to the humeral stem 204 (i.e., to adjust the inclination and/or version angle) to achieve a position that provides the most stability to the joint, thereby preventing dislocation, it is advantageous to provide a mechanism that allows the locking screw 252 to be oriented at angles and rotational positions off-axis (i.e., non-collinearly). It should be understood and appreciated herein that the principles of operations related to the angular variability associated with humeral component 102 as explained above also apply to the reverse tray component 202 described herein. As such, the present invention is not intended to be limited herein.

The aforementioned may, in exemplary forms thereof, be manufactured from titanium, cobalt chrome or stainless steel. However, it should be understood and appreciated herein that any suitable material may be utilized to fabricate the aforementioned components, including, without limitation, plastics, ceramics, metals, and alloys of the foregoing.

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

The terminology used herein is for the purpose of describing particular illustrative embodiments only and is not intended to be limiting. As used herein, the singular forms "a", "an" and "the" may be intended to include the plural forms as well, unless the context clearly indicates otherwise.

The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

The invention claimed is:

1. A variable angle locking system comprising:
a humeral component having an underside at least partially defined by a cavity;
a humeral stem couplable to the humeral component;
a first washer defining a first through-hole, the first washer including a threaded portion;
an adaptor defining a second through-hole, the adaptor including a shelf portion and an elongated second washer, wherein the shelf portion is adapted to be received by the cavity of the humeral component;
a cap having a threaded circumference configured to engage an interior circumferential thread of the shelf portion of the adaptor;

a spring washer positioned between the first washer and the elongated second washer, the spring washer defining a third through-hole; and a screw configured to lock the humeral component to the humeral stem at more than one angle relative to a common axis defined by the first, second and third through-holes, the screw including a head portion having helical threads and an elongated shaft portion extending from the head portion.

2. The variable angle locking system of claim 1, wherein the screw is configured to lock the humeral component to the humeral stem at more than one angle relative to the common axis by lockably mating the helical threads of the screw with the threaded portion of the first washer as the screw is advanced through an opening defined by the first, second and third through-holes.

3. The variable angle locking system of claim 2, wherein the helical threads are configured to lockably mate with the threaded portion of the first washer such that the elongated second washer is positioned at an off-axis angle of up to about 15° in any direction relative to the common axis.

4. The variable angle locking system of claim 1, wherein the cap and the shelf portion of the adaptor each include an inner surface, the inner surfaces collectively defining a spherical cavity that is adapted to receive the head portion of the screw.

5. The variable angle locking system of claim 4, wherein the spherical cavity is configured to partially occupy the first washer, the spring washer and a portion of the elongated second washer.

6. The variable angle locking system of claim 5, wherein the spring washer is configured to provide a tensile force between the first washer and the elongated second washer, the tensile force creating friction between the first and second washers and the inner surfaces defining the spherical cavity.

7. The variable angle locking system of claim 6, wherein the created friction provides an anti-rotational force that prevents the first washer from turning as the helical threads of the screw engage the threaded portion of the first washer.

8. The variable angle locking system of claim 1, wherein the humeral component comprises a humeral head component or a reverse tray component.

9. A variable angle locking system comprising:
a humeral component;
a humeral stem couplable to the humeral component;
a set of stackable washers cooperating to create a common through-hole, the common through-hole defining a common axis therethrough;
a cap having a threaded circumference configured to engage an interior circumferential thread of one of the washers in the set of stackable washers; and
a screw including a head portion having helical threads and an elongated shaft portion extending from the head portion, the screw being configured to lock the humeral component to the humeral stem at more than one angle relative to the common axis as the screw is advanced through the common through-hole;
wherein at least one of the washers in the set of stackable washers is a spring washer.

10. The variable angle locking system of claim 9, wherein at least one of the washers in the set of stackable washers includes a threaded portion configured to mate with the helical threads of the screw.

11. The variable angle locking system of claim 9, wherein the cap is configured to cooperate with one of the washers in the set of stackable washers to collectively define a spherical cavity that is adapted to receive the head portion of the screw.

12. The variable angle locking system of claim 11, wherein the spherical cavity is configured to occupy at least a portion of the set of stackable washers.

13. The variable angle locking system of claim 12, wherein the spring washer is configured to provide a tensile force between two other washers in the set of stackable washers, the tensile force creating friction between the two other washers and the spherical cavity.

14. The variable angle locking system of claim 9, wherein the humeral component comprises a humeral head component or a reverse tray component.

15. A variable angle locking system comprising:
a set of stackable washers cooperating to create a common through-hole, wherein at least one of the washers in the set of stackable washers is a spring washer;
a cap having a threaded circumference configured to engage an interior circumferential thread of one of the washers in the set of stackable washers; and
a screw including a head portion having helical threads and an elongated shaft portion extending from the head portion, the screw being configured to lock a humeral component to a humeral stem at more than one angle relative to a common axis defined by the common through-hole as the screw is advanced therethrough;
wherein the cap is configured to cooperate with one of the washers in the set of stackable washers to collectively define a spherical cavity that is adapted to receive the head portion of the screw and at least a portion of the set of stackable washers.

16. The variable angle locking system of claim 15, wherein the spring washer is configured to provide a tensile force between two other washers in the set of stackable washers, the tensile force creating friction between the two other washers and the spherical cavity.

17. The variable angle locking system of claim 15, wherein the helical threads are configured to lockably mate with a threaded portion of at least one of the washers in the set of stackable washers.

18. The variable angle locking system of claim 15, wherein the humeral component comprises a humeral head component or a reverse tray component.

* * * * *